United States Patent [19]
Krause

[11] Patent Number: 5,458,626
[45] Date of Patent: Oct. 17, 1995

[54] METHOD OF ELECTRICAL NERVE STIMULATION FOR ACCELERATION OF TISSUE HEALING

[76] Inventor: Horst E. Krause, 11 San Jacinto Dr., Galveston, Tex. 77550

[21] Appl. No.: 173,777

[22] Filed: Dec. 27, 1993

[51] Int. Cl.$^6$ ..................................................... A61N 1/18
[52] U.S. Cl. ............................................. 607/50; 128/696
[58] Field of Search ................................... 607/46, 50, 51, 607/52, 25, 42, 62, 63, 72, 73, 74; 128/696, 908, 710

[56] References Cited

U.S. PATENT DOCUMENTS

| 3,650,277 | 3/1972 | Sjostrand et al. | 607/72 |
|---|---|---|---|
| 4,453,547 | 6/1984 | Costel et al. | 607/72 |
| 4,712,558 | 12/1987 | Kidd et al. | 607/50 |
| 4,974,599 | 12/1990 | Suzuki | 128/710 |
| 5,056,519 | 10/1991 | Vince | 607/42 |
| 5,058,584 | 10/1991 | Bowgeois | 607/48 |
| 5,146,918 | 9/1992 | Kallok et al. | 607/42 |

FOREIGN PATENT DOCUMENTS 0533585  3/1993  China .

OTHER PUBLICATIONS

Cook et al., "Vascular Disease of Extremities" NYS J. of Medicine, Mar. 1976.
Dooley et al., "Modification of Blood Flow" Snuth Medical Journal, 1976.
Meglio et al., "Pain Control", Journal of Neurosurgery, 1981.
Kaada, "Promoted Healing of Chronic Ulceration", VASA, 1983.
Kaada, "Vasodilation Induced by Transcutaneous Nerve Stimulation", European Heart Journal, 1982.
Tallis et al., "Spiral Cord Stimulation", Journal of Neurology, Neurosurgery and Psychiatry 1983.
Augustinsson et al., "Epidural Electrical Stimulation", Annals of Surgery, 1985.

Primary Examiner—Lee S. Cohen
Assistant Examiner—Brian M. Green
Attorney, Agent, or Firm—Harrison & Egbert

[57] ABSTRACT

A method of electrical nerve stimulation for acceleration of tissue healing of a patient including the steps of applying a receptor electrode to an area of a body of the patient, applying a stimulating electrode to another area of the body of the patient, transmitting a signal from the receptor electrode to an ECG so as to produce a representation of a cardiac cycle of the patient, and passing an electrical pulse to the stimulating electrode in timed relationship to the representation of the cardiac cycle. A plurality of electrical pulses are passed during each systole period of the cardiac cycle. The stimulating electrode is affixed to an area of the body. A triggering device is connected to the ECG and to the stimulating electrode. The triggering device is programmed so as to pass the electrical pulse repeatedly during identical periods during sequential cardiac cycles.

10 Claims, 2 Drawing Sheets

METHOD OF ELECTRICAL NERVE STIMULATION FOR ACCELERATION OF TISSUE HEALING

TECHNICAL FIELD

The present invention relates to methods for healing tissues. More particularly, the present invention relates to methods and apparatus for electrical stimulation of the nerve system of a human body synchronous to a cardiac cycle or other events in the human body.

BACKGROUND ART

Wounds, skin ulcers and sores of various types and origins require a long time to heal. This healing time results in an equally long period of suffering and a corresponding increase in the cost of medical care. Often, these conditions do not respond to conventional treatment and sometimes lead to a permanent affliction. In some cases, the condition progresses until it becomes necessary to amputate the limb, as in the case of over 35,000 diabetics annually. The danger of permanent affliction or even death is present if response to treatment is poor and gangrenous infection sets in.

Various methods of electrical nerve stimulation are in use for various therapeutic purposes, including the relief of otherwise intractable pain. In particular, electrical nerve stimulators are widely used to induce the contraction of skeletal muscle groups and for the relief of pain by blocking nerve conduction. To accomplish this, electrodes are placed near specific nerves either superficially, percutaneously, or by surgical implantation. The stimulation is accomplished by applying an electrical current to the electrodes. The current is applied in the form of a series of pulses. The duration of an individual pulse, the number of pulses in the series, the time interval of no stimulation after a stimulating pulse series, and the magnitude of the applied electrical current are, in general, variable and are adjusted by the attending physician, therapist, or patient.

In the past, various articles have been written concerning techniques for the electrical stimulation of nerve centers for the purposes of treating the human body. These articles have observed increased blood flow in ischemic areas, the elimination of Raynaud disease symptoms, and an accelerated healing of ulcers of various etiology and ulcers that had not previously responded to conventional treatment. For example, the article of Cook et al , "Vascular Disease of Extremities" *New York State Journal of Medicine*, March 1976, describes the electrical stimulation of the spinal cord and posterior roots. This stimulation was carried out in nine patients with varying degrees of vascular insufficiency in a limb. The electrical stimulation resulted in a striking relief of pain. The infarcted tissue was not restored, but healing was promoted. The results were geared to antidromic stimulation of C fibers in dorsal roots. In this article and in other articles, changes in circulation beyond that obtained with previous regional sympathectomy were observed and identified as the reasons for initiating and promoting healing of wounds and ulcers.

The article by Dooley et al., "Modification of Blood Flow to the Extremities by Electrical Stimulation of the Nervous System," *South Medical Journal*, 1976, described the sixteen patients who had electrical stimulation applied to various portions of the nervous system. Seven of the patients had transcutaneous stimulation applied over the cervical or thoracic spinal cord, peripheral nerves, or lower lumbar region. Eight patients had electrical stimulators implanted over the spinal cord in attempts to relieve intractable pain or some of the symptoms of multiple sclerosis. Another patient had electrical stimulators implanted over the C-6 dorsal roots for small artery disease. The electrical stimulation resulted in significant arterial dilatation and corresponding flow increases. Electrical stimulation applied to the ulnar nerves did not cause arterial dilatation.

The article by Meglio et al., "Pain Control and Improvement of Peripheral Blood Flow Following Epidural Spinal Cord Stimulation," *Journal of Neurosurgery*, 1981, taught the use of epidural spinal cord stimulation for the relief of chronic pain in arteriosclerotic patient. The healing of trophic ulcers was also observed. Hemodynamic studies showed an increase of peripheral blood flow following such stimulation.

The article by B. Kaada, "Promoted Healing of Chronic Ulceration By Transcutaneous Nerve Stimulation," VASA 1983, and by B. Kaada, "Vasodilation Induced By Transcutaneous Nerve Stimulation In Peripheral Ischemia (Raynaud's Phenomenon and Diabetic Polyneuropathy)," European Heart Journal 1982, indicated that marked and prolonged cutaneous vasodilation is produced in patients with Raynaud's Disease and diabetic polyneuropathy in response to distant, low frequency and, in this case, non-traumatic transcutaneous nerve stimulation. This stimulation promoted healing of chronic ulceration of various etiology.

The article by Tallis et al., "Spinal Cord Stimulation In Peripheral Vascular Disease," Journal of Neurology, Neurosurgery, and Psychiatry, 1983, suggested the use of spinal cord stimulation for the treatment of severe intractable symptoms of arterial disease. The electrical stimulation resulted in small increases in cutaneous and muscle blood flow. The improvements were maintained as long as spinal cord stimulation was continued.

In the article by Augustinsson et al., "Epidural Electrical Stimulation in Severe Limb Ischemia," Annals of Surgery, 1985, it was suggested that epidural spinal electrical stimulation could improve peripheral circulation in the cases of ischemic pain, skin ulcerations, and gangrene. It was found that this electrical stimulation was very promising in severe limb ischemia where reconstructive surgery was impossible or had failed. Approximately fifty percent of previously unresponsive ulcers could be healed. Only 38% of the treated patients had an amputation as compared to 90% in a comparable group of unstimulated patients.

Hotta et al. report about observations that provide some details about the mechanism behind the increase of the flow rate in the extremities in his article "Stimulation of Lumbar Sympathetic Trunk Produces Vasoconstriction of the Vasa Nervorum in the Sciatic Nerve Via α-Adrenergic Receptors in Rats", *Neuroscience Letters*, 1991. The unilateral electrical stimulation of the lumbar sympathetic trunk at low frequencies produced a substantial increase in the flow of blood in the vasa nervorum of the sciatic nerves in the hind legs of rats. This period of increased flow was followed by a moderate decrease of this flow in the leg on the side of stimulation while only the increase of flow was observed in the leg on the other side. The increase of flow, and only this increase, could still be observed in both legs after local sympathetic denervation. The mean arterial pressure remained elevated throughout the stimulation period in every one of the above experimental conditions. The observed increase of flow in the extremities was a passive response due to a central systemic constriction and not to peripherally located nervous responses. Thus the flow rate in the vasa nervorum, or other compromised vascular beds, can be maximized by selecting the proper frequency of stimulation, duration of stimulation, and should be further augmented by synchronisation with systolic pressure peaks.

In his extensive publication "Circulatory Response to Stimulation of Somatic Afferents", *Acta. Physiol. Scandi*, 1962, Johansson confirms the interpretation by Hotta by observing substantial increases of the resistance to flow, and concomitant arterial pressure rise, in the kidneys in response to afferent electrical stimulation of peripheral somatic nerves. The same observation was made by other authors (e.g., Olov Celander, "The Range of Control Exercised by the Sympathetic Adrenal System", *Acta. Physiol. Scandi*, 1954) for other internal organs including the observation of a frequency dependent degree of resistance elevation.

As can be seen, in the past, most physicians and manufacturers have viewed nerve stimulation as strictly nervous events in the afflicted area. These physicians and manufacturers have generally ignored the promotion of healing through increased circulation produced by 637 synchronized nerve stimulation".

It is an object of the present invention to provide a method for the acceleration of tissue healing.

It is another object of the present invention to provide a method for increasing blood flow through deprived tissues.

It is a further object of the present invention to provide a method that correlates electrical stimulation of nerves to the action of the heart or other internal or extracorporeal events.

These and other objects and advantages of the present invention will become apparent from a reading of the attached specification and appended claims.

SUMMARY OF THE INVENTION

The present invention is a method of electrical nerve stimulation for the acceleration of tissue healing of a patient. The method of the present invention includes the steps of: (1) applying a receptor electrode to an area of the body of the patient; (2) applying a stimulating electrode to another area of the body of the patient; (3) transmitting a signal from the receptor electrode to an electrocardiograph (ECG) so as to produce a representation of a cardiac cycle (ECG) of the patient; and (4) passing an electrical pulse to the stimulating electrode in timed relationship to the representation of the cardiac cycle. As used herein, the terms "electrode" and "pulse" are inclusive of the plural "electrodes" and "pulses", respectively.

In particular, the cardiac cycle shows a systolic period and a diastolic period. The step of passing includes passing a plurality of electrical pulses during the systolic period of the cardiac cycle in the preferred embodiment. This plurality of electrical pulses occur throughout a selected period of the cardiac cycle, such as the systolic period.

The step of applying the stimulating electrode includes affixing the stimulating electrode to an area of the body other than the tissue to be healed. In particular, in the preferred embodiment of the present invention, the stimulating electrode is applied so as to result in the stimulation of the vascular smooth muscles of the splanchnic circulatory system. The electrical pulse is passed so as to be of sufficient energy such that the vascular smooth muscles are contracted so as to increase hydraulic resistance of at least a portion of the splanchnic circulatory system.

In the present invention, the step of applying a receptor includes applying a plurality of receptor electrodes to the patient. The step of transmitting includes connecting the receptor electrodes to an electrocardiograph, amplifying an electrical signal of the heart so as to produce the representation of the cardiac cycle, and creating a graphical illustration of the cardiac cycle.

In the method of the present invention, a triggering device is connected to the ECG and to the stimulator. The triggering device is programmed so as to pass the electrical pulse repeatedly. The stimulator serves to transmit stimulating pulses to the patient via the stimulating electrode. The programming of the stimulator can include adjusting the magnitude of the voltage or current of the electrical pulse. The programming can include adjusting the length of time of the pulse or the amount of time between consecutive pulses. The step of programming can further include adjusting the amplitude or frequency modulation of a plurality of electrical pulses within a single pulse train.

DETAILED DESCRIPTION OF THE INVENTION

Figure 1:
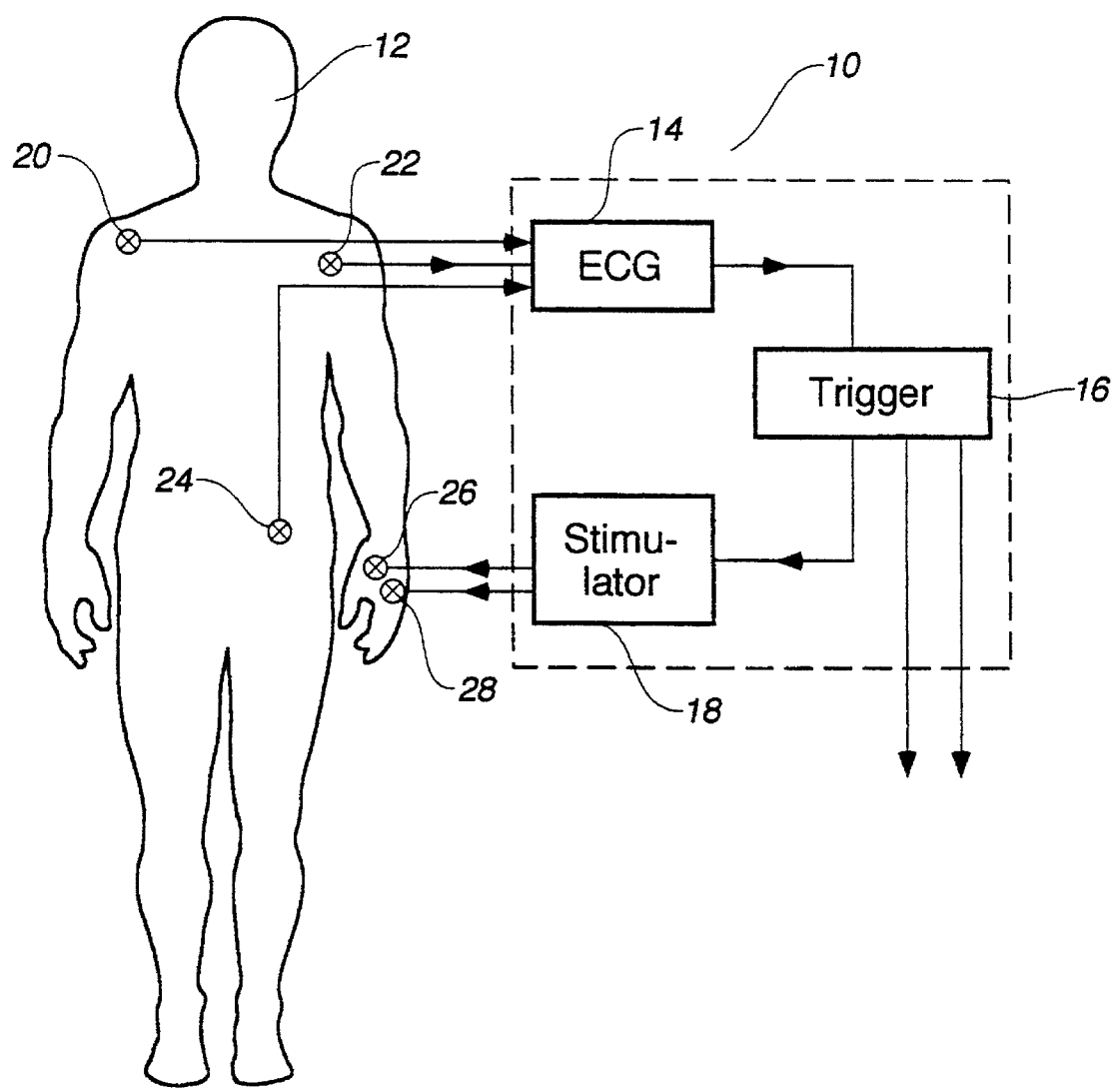
FIG. 1 is a schematic illustration of the method of the present invention.

Referring to FIG. 1, there is shown at 10, the system of the present invention for the electrical stimulation for the acceleration of tissue healing of the patient 12. The system 10 includes the ECG 14, a trigger device 16, and a stimulator 18. Each of these elements are interactive so as to provide the required electrically stimulating effect for the purpose of healing the tissue of patient 12.

Initially, the receptor electrodes 20, 22, and 24 are applied to the patient 12. The purpose of the electrodes 20, 22, and 24 is to transmit electrical signals generated by the heart and to communicate such signals to the electrocardiograph via the connecting cables. Within the scope of the present invention, a single receptor electrode could be used. However, in the preferred embodiment of the present invention, a plurality of such electrodes are used so as to provide a representative reading to the electrocardiograph.

The electrodes 20, 22, and 24 sense the potential of the electrical currents generated by the heart and communicate them to the electrocardiograph 14. The electrocardiograph amplifies these potentials greatly. These potentials will vary in magnitude in a typical fashion during the course of a cardiac cycle.

Figure 2:
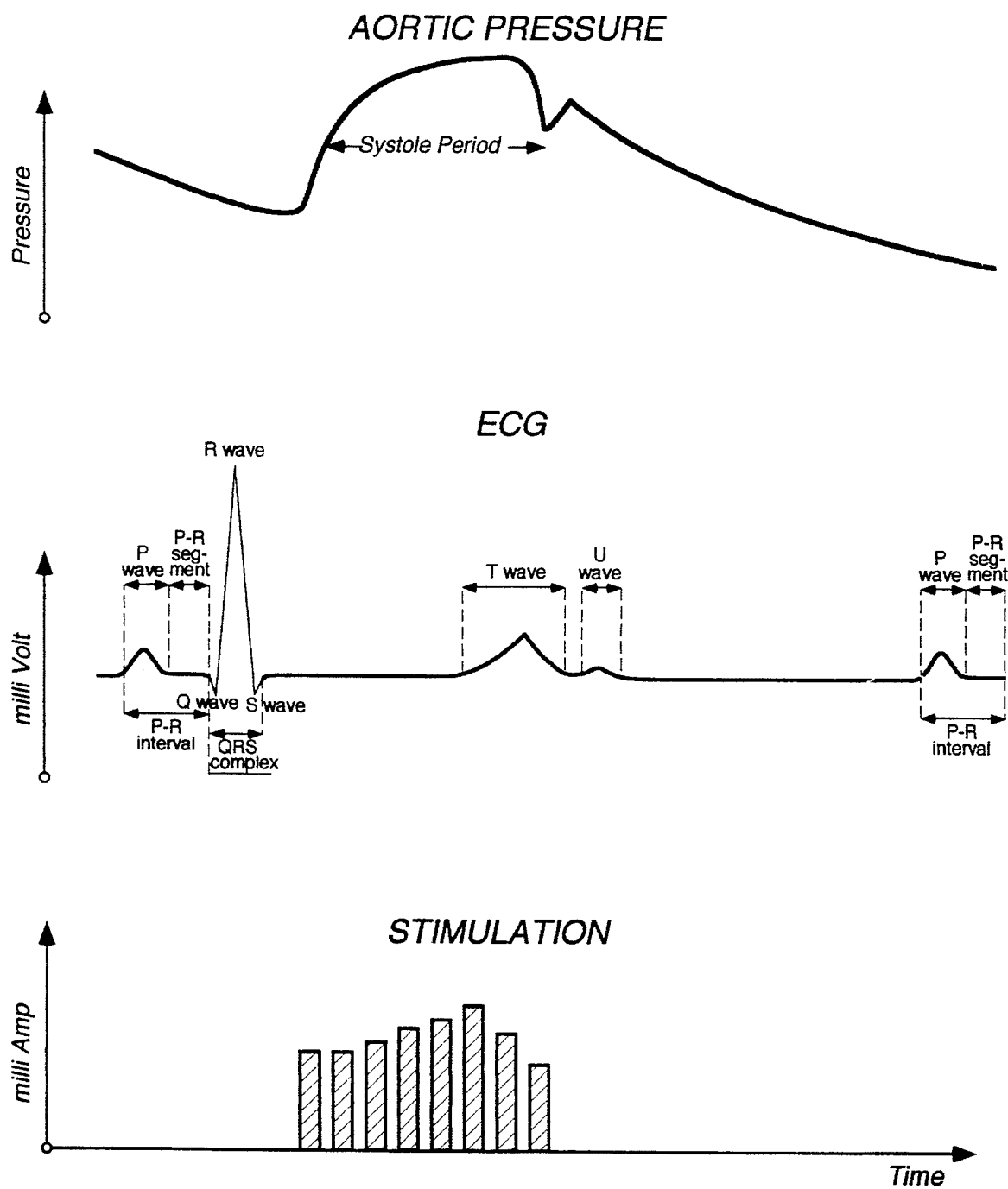
FIG. 2 is a multiple graphical illustration of the method of the present invention in relation to aortic pressure and the ECG graph.

The electrocardiograph will produce a graphic recording of the cardiac cycle in an electrocardiogram (ECG). FIG. 2 illustrates such an ECG, together with the simultaneously occurring variation of the aortic pressure during the course of the same cardiac cycle. With reference to FIG. 2, it can be seen that the electrocardiogram is composed of three very distinct events. These events are the P wave, the so-called QRS complex, and the T wave. The P wave occurs at the beginning of each contraction of the atria. The QRS complex occurs at the beginning of each contraction of the ventricles. The T wave occurs as the ventricles recover electrically and prepare for the next contraction. It is, therefore, apparent that these distinct features of the ECG are uniquely related to the pumping action of the heart and, as a consequence, uniquely related to the variations of the blood pressure and blood flow during the course of one cardiac cycle. In FIG. 2, it can be seen that the systolic period corresponds generally to the period between the end of the QRS complex period and the peak of the T wave.

In the preferred embodiment of the present invention, the electrocardiograph 14 provides the ECG as an electrical input to the trigger component 16. It is evident from an inspection of the ECG in FIG. 2 that considerable and characteristic variations occur that are typical for certain portions and instances within one cardiac cycle. For example, the peak voltages of all three above-mentioned sections (P wave, QRS complex, T wave) are significantly different. Secondly, the slope of the QRS complex, for instance, differs considerably from that of the P wave or the T wave. The slopes, as well as the voltages, assume both positive and negative values during the course of a cardiac cycle. Therefore, the peak of a wave, the combination of a voltage and the simultaneously existing rate of its change (slope), or only a voltage, should be characteristic for most instances during these three segments and can therefore be used to identify the instantaneous status of the ventricles within a cardiac cycle. The possibility of ambiguity of identification can be reduced by also considering a third variable, besides instantaneous voltage and slope. Such a variable could be the time interval between the occurrence of a very distinct and unique point, such as the greatest negative voltage preceded by a sharp negative slope followed by a sharp positive slope (also designated as the Q instant), and the voltage and slope at the instant of recording. Various algorithms, using such variables as inputs, as well as sophisticated mathematical transforms, filtering, correlation, and signal identification methods, can be utilized to numerically correlate pertinent instances as to their position within the period of one cardiac cycle.

The trigger device 16 is a processor which will receive the ECG 14 as input and process it in the manner described above so as to activate the stimulator 18 at the desired instance and for the desired period of time. The trigger device 16 can also incorporate several channels and outputs so as to activate a multitude of devices at individual instances and for individual intervals. In the method of the present invention a plurality of stimulating electrodes 26 and 28 are applied to the body of the patient 12. Within the concept of the present invention, the stimulating electrodes 26 and 28 are positioned on certain areas of the body of the patient 12 other than the tissue to be healed. The stimulator electrodes 26 and 28 receive their electrical pulse from the stimulator 18. Trigger device 16 can also transmit signals to additional stimulators or other devices.

In the present invention, the cardiac cycle will have a systolic period and a diastolic period. The stimulator 18 will pass electrical pulses during the systole period of the cardiac cycle. As can be seen in FIG. 2, the electrical stimulation is graphically illustrated in relation to the systolic period. It can also be seen in FIG. 2 that a plurality of electrical impulses occur throughout an entire systolic period. The triggering device 16 is programmed so as to pass the triggering pulse repeatedly at identical instances during sequential cardiac cycles. Specifically, the electrical stimulation that can be used for stimulation of the vascular smooth muscles of the splanchnic circulatory system is 60 to 70 volts at currents of 15 to 30 mA. The pulse length can be between 0.05 to 1.5 milliseconds.

In the specific embodiment of the present invention, the stimulating electrodes 26 and 28 are placed over or on selected nerves and connected to the stimulator 18. Upon activation of the system 10, a preprogrammed personalized sequence of electrical impulses is delivered from the stimulator 18 to the nerve simultaneously with the onset of cardiac systole. The electrical impulses will continue to be delivered throughout this period.

The electrical stimulus is structured such that the vascular smooth muscles of the splanchnic circulatory system are innervated, contract, and increase the hydraulic resistance of this part of the systemic circulation. As a consequence, the amount of blood flowing into diseased extremities is increased. In particular, the systolic peak pressure is increased in the diseased extremities because the elevated splanchnic hydraulic input resistance reflects a greater portion of the pulsatile pressure and flow components back into the remaining part of the systemic circulatory system. This increases the pulsatile energy in that part by as much as sixty percent. The elevation of the pulse pressure drives more blood through pathologically underperfused blood vessels, generates collateral vessels and, by delivering oxygen and nutrients, accelerates and enables the healing process.

The endothelial cells release vasodilatory substances, such as prostacyclin, while being mechanically stimulated by blood pressure variations. Therefore, the increase in the flow of blood is further advanced by the restoration and elevation of pressure pulsations and the resulting prostacyclin release in and around tissues and organs with obliterative vascular condition.

This operation of the present invention constitutes but one preferred example of it. The output of the trigger device allows the medical personnel to enter one, two, or three variables (or a code number), or to place an indicator within a display of the ECG at a point at which they choose to have the trigger device 16 activate the stimulator 18. It also allows the medical personnel to select a second point or time interval at which they choose to terminate the stimulation until the same sequence is automatically resumed during the following cardiac cycles. The triggering of the stimulator 18 at the selected instances and in synchrony with the ECG or any other internal or external event constitutes an improvement over prior methods of treatment and also introduces new possibilities of treatment.

The stimulator 18, upon triggering, provides a structured stimulus to a selected nerve or bundles of nerves via electrodes which are located on the patient's body surface, or are placed percutaneously, or by surgical implantation. Both the location of the electrodes and the structure of the stimulus are specific as to the pathological condition of the patient. The stimulator, therefore, is equipped for producing various types of stimulation structures in order to treat a variety of pathological conditions. Therefore, the variables that are adjustable by the medical personnel include the shape of the stimulating pulses, the magnitude of their current or voltage, the interval of time of an individual pulse, the interval of time between two consecutive pulses, the number of such pulses within a train of pulses, the amplitude and/or frequency modulation of the pulses within one train, and the time interval between trains of pulses. Since the structure of stimulation is often specific for the pathological condition and/or the patient, the stimulator 18 is equipped with a computer so that, among other functions, the optimal structure, after being determined by the clinic, can be programmed into the stimulator 18. In such a situation, the patient can then use the stimulator safely on his or her own, while performing most of the daily routines.

The present invention is essentially an electrical nerve stimulation system that incorporates an electrocardiograph in communication with a patient and in communication with an electric signal identifying device. This device identifies select points on the electrocardiogram and provides a triggering impulse which activates an electrical nerve stimulator in timed relation with the heart or other intracorporeal or extracorporeal events. The stimulator provides a stimulus which is structured to elevate the arterial blood pressure pulse and this effect is maximized by the system's capability to stimulate synchronously with and during the cardiac systole. Thus, the flow of blood through pathologically underperfused tissues is increased, collateralization is proliferated, and healing of wounds, ulcers, and neuropathic conditions is accelerated and made possible in previously unresponsive cases.

The present invention is also an electrical nerve stimulation system which can promote healing in relation to an extracorporeal or an internal event relative to the patient. In this configuration, the receptor electrode is applied to a source indicative of the extracorporeal or internal event. The processor is then used to produce a representation of such event. Electrical pulses are then passed to the stimulating electrodes in timed relationship to the representation of the event.

The foregoing disclosure and description of the invention is illustrative and explanatory thereof. Various changes in the steps of the described method may be made within the scope of the appended claims without departing from the true spirit of the invention. The present invention should only be limited by the following claims and their legal equivalents.

I claim:

1. A method for acceleration of tissue healing of a patient comprising the steps of:

applying a receptor electrode to an external surface of a body of the patient, said receptor electrode for sensing an electrical parameter from said external surface;

applying a stimulating electrode to another external surface of the body of the patient;

transmitting a signal from said receptor electrode to a monitor so as to produce a representation of a cardiac cycle of the patient; and passing a plurality of electrical pulses to said stimulating electrode in timed relationship to said representation of said cardiac cycle, said cardiac cycle having a systolic period and a diastolic period, said step of passing comprising:

passing a plurality of electrical pulses during said systolic period of said cardiac cycle, said plurality of electrical pulses occurring throughout an entire systolic period.

2. The method of claim 1, said step of applying a receptor electrode comprising:

applying a plurality of receptor electrodes to the patient.

3. The method of claim 2, said step of transmitting comprising the steps of:

connecting said receptor electrodes to an electrocardiograph;

amplifying an electrical signal of the heart so as to produce said representation of the cardiac cycle; and creating a graphical illustration of a cardiac cycle.

4. A method for acceleration of tissue healing of a patient comprising the steps of:

applying a receptor electrode to an external surface of a body of the patient, said receptor electrode for sensing an electrical parameter from said external surface;

affixing a stimulating electrode to an external surface of the body other than the tissue to be healed, said stimulating electrode being affixed adjacent a nerve suitable for stimulating vascular smooth muscles of the splanchnic circulatory system;

transmitting a signal from said receptor electrode to a monitor so as to produce a representation of a cardiac cycle of the patient; and passing a plurality of electrical pulses to said stimulating electrode in timed relationship to said representation of said cardiac cycle.

5. The method of claim 4, said step of passing a plurality of electrical pulses comprising:

passing an electrical pulse to said nerve of sufficient energy such that said vascular smooth muscles are contracted so as to increase hydraulic resistance of a portion of the splanchnic circulatory system.

6. A method for acceleration of tissue healing of a patient comprising the steps of:

affixing a stimulating electrode to an external surface of a body of the patient adjacent to a nerve suitable for stimulating vascular smooth muscles of the splanchnic circulatory system of the patient;

applying electrical pulses to said stimulating electrode so as to contract said vascular smooth muscles; and repeating said electrical pulses over a desired period of time, said electrical pulses applied only during a systole period of a cardiac cycle, said electrical pulses applied repeatedly during said systole period.

7. The method of claim 6, further comprising the step of:

monitoring a cardiac cycle of the patient so as to determine the systole period of said cardiac cycle.

8. The method of claim 7, said step of monitoring comprising:

applying a receptor electrode to the patient; and transmitting a signal from said receptor electrode to an ECG so as to produce a representation of said cardiac cycle of the patient.

9. The method of claim 8, said step of applying a receptor electrode comprising:

connecting said ECG to a triggering device; and programming said triggering device so as to pass said electrical pulses during said systole period of said cardiac cycle.

10. The method of claim 6, said vascular smooth muscles being at a different location on the body than the tissue to be healed.

* * * * *